(12) United States Patent
Gaetani

(10) Patent No.: US 8,252,309 B2
(45) Date of Patent: *Aug. 28, 2012

(54) DIETARY SUPPLEMENT ENERGY-PROVIDING TO SKELETAL MUSCLES

(75) Inventor: Franco Gaetani, Ariccia (IT)

(73) Assignee: Sigma-Tau Industrie Farmaceutiche Riunite SpA, Rome (IT)

( * ) Notice: Subject to any disclaimer, the term of this patent is extended or adjusted under 35 U.S.C. 154(b) by 1044 days.

This patent is subject to a terminal disclaimer.

(21) Appl. No.: 11/253,806

(22) Filed: Oct. 20, 2005

(65) Prior Publication Data

US 2006/0057188 A1 Mar. 16, 2006

Related U.S. Application Data

(60) Continuation-in-part of application No. 11/174,553, filed on Jul. 6, 2005, now abandoned, which is a continuation of application No. 10/341,249, filed on Jan. 14, 2003, now abandoned, which is a division of application No. 09/980,278, filed as application No. PCT/IT01/00167 on Mar. 30, 2001, now abandoned.

(30) Foreign Application Priority Data

Apr. 4, 2000 (IT) .............................. RM2000A0165

(51) Int. Cl.
| A61K 47/00 | (2006.01) |
| A61K 38/43 | (2006.01) |
| A61K 31/525 | (2006.01) |
| A01N 43/60 | (2006.01) |

(52) U.S. Cl. ...................... 424/439; 424/94.1; 514/251

(58) Field of Classification Search .................. 424/439, 424/94.1; 514/251
See application file for complete search history.

(56) References Cited

U.S. PATENT DOCUMENTS

| 3,219,454 A | 11/1965 | Howard et al. |
| 3,689,641 A | 9/1972 | Spangler et al. |
| 4,237,118 A | 12/1980 | Howard |
| 5,466,469 A * | 11/1995 | Kuhrts .......................... 424/451 |
| 5,753,703 A | 5/1998 | Cavazza et al. |
| 5,866,537 A | 2/1999 | Bianchi |
| 5,889,062 A | 3/1999 | Hoppe et al. |
| 5,952,379 A * | 9/1999 | Fassi .............................. 514/561 |
| 5,976,568 A | 11/1999 | Riley |
| 6,562,869 B1 | 5/2003 | Hamilton et al. |

FOREIGN PATENT DOCUMENTS

| WO | WO 98/43499 | 10/1998 |
| WO | WO 99/53921 | 10/1999 |

OTHER PUBLICATIONS

Hultquist et al, Evidence That NADPH-Dependent Methemoglobin Reductase and Administered Riboflavin Protect Tissue From Oxidative Injury, 1993, Wiley-Liss, pp. 1-2.*
Schonekess et al, Propionyl L-Carnitine Improvement of Hypertrophied Heart Function Is Accompanied by an Increase in Carbohydrate Oxidation, 1995, Circulation Research, 77, pp. 726-734 (Journal Pages), (Note: pp. 1-18 are the only attached pages—from online reference).*
Berge et al, Pharmaceutical Salts, 1977, Journal of Pharmaceutical Sciences, vol. 66, No. 1, pp. 1-19.*
Rudnic et al, Oral Solid Dosage Forms, 1990, Remington's Pharmaceutical Sciences, 18th, pp. 1633-1652, 1654-1665, and 1 bibliographic page (33 pages in all).*
Supplee et al, Interrelated Vitamin Requirements: Kidney Damage, Adrenal Hemorrhage and Cardiac Failure Correlated with Inadequacy of Pantothenic Acid, 1942, Endocrinology, vol. 30, No. 3, Abstract, pp. 1-2.*
Supplements:Creatine, 1999, Integrative Medicine Communications, pp. 1-3.*
Siscovick et al, The Incidence of Primary Cardiac Arrest during Vigorous Exercise, 1984, The New England Journal of Medicine, 311, pp. 874-877.*

* cited by examiner

*Primary Examiner* — David J Blanchard
*Assistant Examiner* — Trevor Love
(74) *Attorney, Agent, or Firm* — Lucas & Mercanti, LLP

(57) ABSTRACT

Dietary supplements—providing energy and strengthening skeletal muscles and facilitating skeletal muscles ability to sustain prolonged periods of physical activity—containing propionyl-L-carnitine or one of its salts, coenzyme $Q_{10}$, nicotinamide, riboflavin, pantothenic acid and optionally other components such as amino acids and creatines.

8 Claims, 3 Drawing Sheets

DIETARY SUPPLEMENT ENERGY-PROVIDING TO SKELETAL MUSCLES

CROSS REFERENCE TO RELATED APPLICATION

This application is a continuation-in-part of application Ser. No. 11/174,553, filed Jul. 6, 2005, now abandoned, which in turn is a continuation of application Ser. No. 10/341,249 filed Jan. 14, 2003, now abandoned, which in turn is a division of application Ser. No. 09/980,278 filed Dec. 3, 2001, now abandoned, which in turn is a U.S. national phase of PCT/IT01/00167 filed Mar. 30, 2001, the entire content of each of which is hereby incorporated by reference in this application.

The present invention relates to an energy-giving dietary supplement aimed particularly at facilitating the adaptation of skeletal and cardiac muscle of subjects engaging in physical and/or recreational activity that may be particularly intense and prolonged. Anyone engaging in sports activities, whether professionally or as an amateur, wishes to achieve as soon as possible and maintain for as long as possible the maximum degree of adaptation of the skeletal muscles to the ability to sustain prolonged periods of intense physical activity.

The quest for optimal physical fitness may favour the inappropriate use of drugs, particularly steroids. It is well known that such drugs may enhance protein synthesis and consequently boost the growth of muscle masses to a greater extent than can be achieved by training and dieting. The use of such drugs, however, is unquestionably damaging to health as well as being illegal when practised in professional sport.

It is, therefore, obvious that the only correct way to achieve the abovementioned goal consists in engaging in lengthy training schedules backed up by suitable, properly supplemented diets.

Thus, more or less recently, various dietary supplements have been proposed aimed at reinforcing the diets of individuals engaging in intense physical activity whether at the professional or amateur level.

The vast majority of these supplements devote particular attention to the metabolism of the skeletal muscle which requires a vast range of nutrients for protein synthesis, mainly including amino acids. In fact, since almost all amino acids, whether essential or non-essential, are substrates needed by the muscle cells for such synthesis, dietary supplements have been marketed now for some time containing mixtures of amino acids in various weight-to-weight ratios in combination with other active ingredients and nutrients (see, for example, U.S. Pat. Nos. 4,687,782 and 5,292,538).

With other dietary supplements, on the other hand, the attention is focused rather on the production of energy and thus of ATP. The ingredients characterizing these supplements are therefore mainly coenzyme $Q_{10}$ and creatine.

Coenzyme $Q_{10}$ plays a fundamental role in the transport of electrons along the mitochondrial respiratory chain, which is necessary for the energy transformations needed for ATP production.

The physiological function of creatine, which is partly biosynthesized in the liver and kidneys and partly ingested with the diet, is also extremely important in energy terms: in muscle, but also in the brain, liver and kidneys, creatine reversibly takes up the phosphoric group of ATP and plays a role as a reserve of phosphoric radicals rich in energy.

The importance of this reaction stems from the fact that ATP cannot accumulate in tissues above a very modest limit. It is the phosphocreatine present in tissues in amounts roughly five-fold higher than ATP, that ensures its supply. In fact, after even only moderate physical exercise, phosphocreatine diminishes in skeletal muscle to a much more marked extent than ATP, demonstrating that phosphocreatine rephosphorylates ATP, as the ATP is dephosphorylated. When the rate of metabolic production of ATP exceeds its rate of use, phosphocreatine is formed. Phosphocreatine thus constitutes a store of immediately utilizable energy suitable for "buffering" energy needs above the ATP synthesis rate in phosphorylative metabolic processes.

In brief, with the existing dietary supplements there is a tendency, on the one hand, to enhance muscle mass and, on the other, to constitute energy reserves that make available immediately "consumable" energy when the intensity of the physical effort requires it.

The muscle enhancement and the increased availability of energy favoured by these known food supplements may, however, cause even severe side effects, particularly in subjects who, since they do not practise sport professionally and thus are not subjected periodically to thorough check-ups, may be induced to engage in physical performances exceeding their physiological resistance limits without them necessarily perceiving this situation.

Such subjects constitute the majority of users of dietary supplements and a considerable proportion of them are made up of individuals who are no longer young or may be decidedly elderly, who very rarely undergo medical check-ups to ascertain their suitability for the physical activity they undertake and to establish the limits of intensity and effort beyond which it is dangerous to push oneself.

Since it is particularly the cardiovascular system that is most strongly stressed by any type of physical or sporting activity, there can be little doubt as to the obvious danger to which these users are exposing themselves, in that their propensity to sustain loads of fatigue and physical stress disproportionate to the state and integrity of the cardiovascular apparatus may be increased considerably by consuming such energy-giving supplements.

There is, therefore, a perceived need for a dietary supplement which, on the one hand, has an energy-giving and strengthening effect on skeletal muscle and, on the other, exerts at the same time a protective, tonic effect on the user's cardiovascular apparatus.

The aim of the present invention is to provide just such a dietary supplement.

BRIEF DESCRIPTIONS OF DRAWINGS

Figure 1:
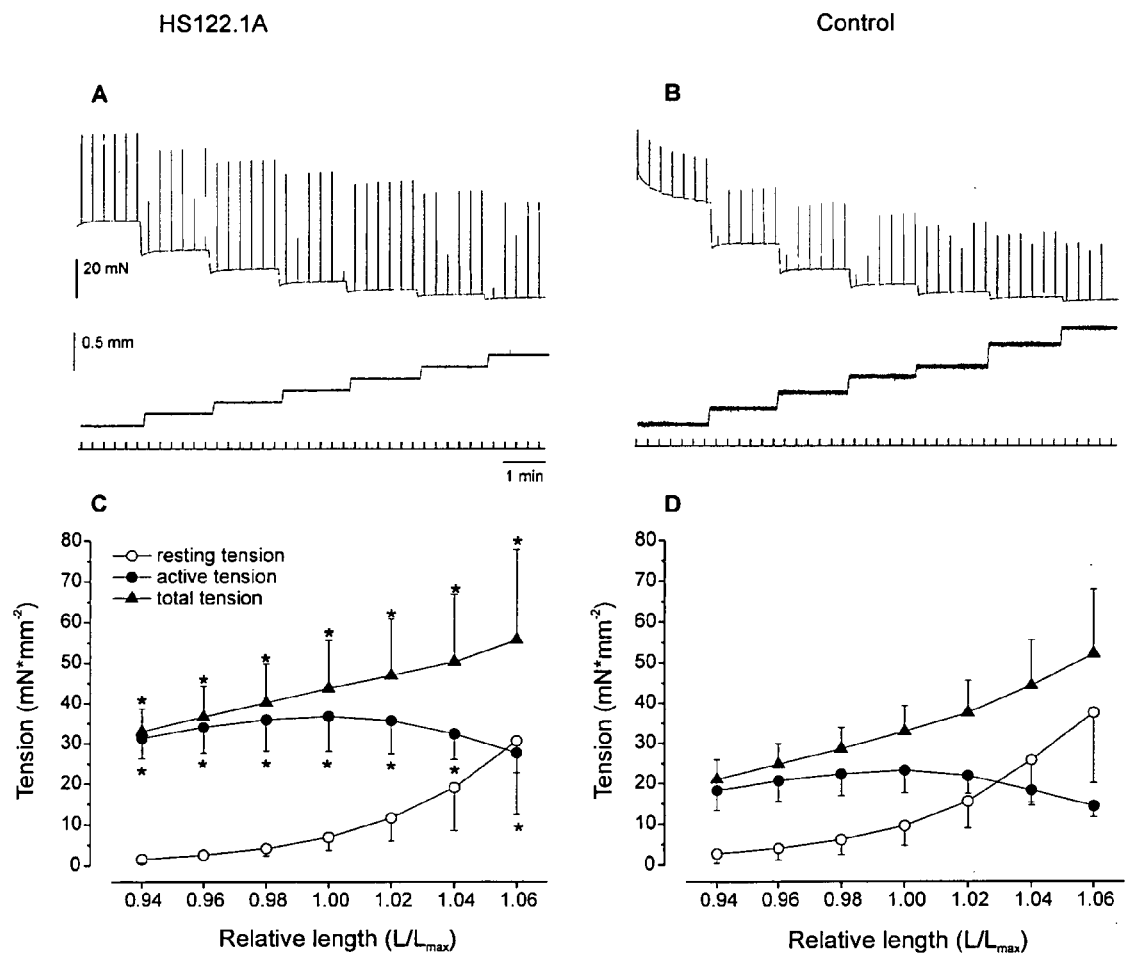
FIG. 1 represents the length-tension relations on LVPM from HS122.1A-supplemented and control rats.

One object of the present invention is, therefore, a dietary supplement endowed with a potent strengthening and energy-giving effect on skeletal muscle and, at the same time, a protective, tonic effect on the cardiovascular apparatus of individuals engaging in sporting and/or recreational activities that may require intense, prolonged physical effort, the characterizing components of which, in combination or packaged separately, comprise:

a) propionyl L-carnitine or one of its pharmacologically acceptable salts;
b) coenzyme $Q_{10}$;
c) riboflavin, and
d) pantothenic acid.

The weight-to-weight ratio of components (a):(b):(c):(d) ranges from 10:0.04:0.08:0.4 to 1:4:4:20 and preferably from 10:2:2:2 to 1:1:1:5.

The activity of the "carnitines" in general, and of propionyl L-carnitine in particular, on lipid metabolism is well known, as is their antiatherosclerotic action and their action on lipid metabolism disorders.

Propionyl L-carnitine, however, differs from the other "carnitines" in its specific cardiovascular activity, despite participating, like the other "carnitines", above all at mitochondrial level, in the important metabolic role related to the β-oxidation of fatty acids and ATP synthesis.

Propionyl L-carnitine takes part in all the metabolic activities characteristic of the "carnitines", but, unlike the others, presents a more pronounced activity at the vascular level, and particularly at the level of the peripheral circulation, thus presenting itself as a valid therapeutic agent for the prevention and treatment of various peripheral vasculopathies. Propionyl L-carnitine is also superior to the other carnitines in conditions in which the other carnitines are unable to act, and this particular feature is related to its more direct metabolic intervention in the processes of energy utilization at the mitochondrial level and to the presence of the propionyl group which distinguishes its pharmacological effect from that of other similar molecules to such an extent as to make it a chemical entity in its own right, with superior and different properties to those of the other carnitines.

Propionyl L-carnitine is a naturally occurring component of the pool of carnitines and is synthesized by means of carnitine acetyl-transferase starting from propionyl-Coenzyme A.

Its administration to human subjects leads to an increase in plasma concentrations of propionyl L-carnitine which in turn causes an increase in plasma concentrations of L-carnitine which regulate its content in the cells with an increase in their oxidative effect on fatty acids and utilization of glucose. In addition, muscular carnitine transferase possesses a greater affinity for propionyl L-carnitine than for L-carnitine, and consequently propionyl L-carnitine possesses a higher degree of specificity for cardiac and skeletal muscle.

Transporting the propionyl group, propionyl L-carnitine increases the uptake of this component by the muscle cells, particularly those of the myocardium. This may be of particular importance, since propionate can be used by the mitochondria as an anaplerotic substrate and supply energy in anaerobic conditions. It should be recalled that propionate cannot be used alone on account of its side effects.

Apart from these metabolic effects, it should also be recalled that, owing to its alkanoyl chain, propionyl L-carnitine exerts a specific pharmacological action by activating peripheral vasodilatation and myocardial inotropism in conditions in which the other carnitines are inactive.

In addition to propionyl L-carnitine, the dietary supplement can further comprise a "carnitine" selected from the group consisting of L-carnitine, acetyl L-carnitine, valeryl L-carnitine, isovaleryl L-carnitine and butyryl L-carnitine or their pharmacologically acceptable salts.

What is meant by a pharmacologically acceptable salt of L-carnitine or of an alkanoyl L-carnitine is any salt of these with an acid which does not give rise to unwanted toxic or side effects. These acids are well known to pharmacologists and to experts in pharmaceutical technology.

Examples of such salts, but by no means exclusively these, are the following: chloride; bromide; iodide; aspartate, acid aspartate; citrate, acid citrate; tartrate; phosphate, acid phosphate; fumarate, acid fumarate; glycerophosphate; glucose phosphate; lactate; maleate, acid maleate; mucate; orotate; oxalate, acid oxalate; sulphate, acid sulphate; trichloroacetate; trifluoroacetate and methane sulphonate.

A list of FDA-approved pharmacologically acceptable acids is given in Int. J. Pharm., 33, 1986, 201-217, the latter publication being incorporated in the present description for reference purposes.

For the preparation of solid administration forms, such as, for example, tablets, pills, capsules and granulates, the use of non-hygroscopic salts is preferred. The preferred non-hygroscopic salts of propionyl L-carnitine and of any other alkanoyl L-carnitines present are the mucates (or galactarates), disclosed in U.S. Pat. No. 5,952,379 which is incorporated herein by reference.

Whenever, in the above-mentioned solid administration forms, L-carnitine is also present, the preferred salt of this carnitine is the acid fumarate described in U.S. Pat. No. 4,602,039 which is incorporated herein by reference.

In addition to its characteristics of stability and lack of hygroscopicity, L-carnitine fumarate exerts a double protective action with regard to protein metabolism: through a direct increase in intermediate metabolism, it indirectly stimulates protein biosynthesis and, as a result of the mobilization of fatty acids, induces a sparing/protective effect on the muscle protein components.

The dietary supplement according to the invention may further comprise one or more of the following components: f) an amino acid selected from the group consisting of valine, leucine and isoleucine or mixtures thereof; g) a creatine selected from the group consisting of creatine and phosphocreatine or mixtures thereof.

The dietary supplement of the present invention in unit dose form contains:

| propionyl L-carnitine | from 50 mg | to 2,000 mg |
| coenzyme $Q_{10}$ | from 5 mg | to 200 mg |
| riboflavin | from 5 mg | to 200 mg |
| pantothenic acid | from 10 mg | to 1,000 mg. |

For example, a formulation suitable for tablets is the following:

| propionyl L-carnitine | 250 mg |
| coenzyme $Q_{10}$ | 20 mg |
| riboflavin | 20 mg |
| pantothenic acid | 20 mg |

The supplement may further comprise mineral salts, such as, for example, disodium citrate, monopotassium phosphate, calcium lactate and magnesium taurate. The dietary supplement of the present invention is suitable for oral administration. The supplement, even when comprising the above-mentioned amino acids, must not be used as a single or main source of nutrition on a day-to-day basis.

The complementary part of the diet will, therefore, consist of appropriate amino acids, carbohydrates, lipids, vitamins and minerals.

The amount of dietary supplement taken daily may vary within broad limits, depending, for example, on the subject's age and weight, or upon the intensity and complexity of the training schedule or the physical activity the individual engages in.

The potent energy-giving effect on skeletal muscle and, at the same time, the protective effect on the cardiovascular system that is achieved with the dietary of the present invention has been shown by several pharmacological tests (some of which are described here below) selected in such a way as to be strongly predictive for the practical use of the supplement in the human field. In these tests, the animals treated with a composition according to the invention were administered the tablet formulation previously described at the dose of 50 mg/kg/day for seven weeks.

EXAMPLE 1

Improvement of Cardiac Mechanics by a Composition Composed of Propionyl L-Carnitine, Coenzyme $Q_{10}$, Riboflavin and Pantothenic Acid in the Rat The mechanical effects of long term (7 weeks) treatment with a co-formulation of Propionyl L-carnitine, Coenzyme $Q_{10}$, Riboflavine and Pantothenic acid (this composition in the following will be mentioned as "HS122.1A"), were studied on rat isolated left ventricular papillary muscle (LVPM).

The active length-tension curve for HS122.1A-treated LVPM was elevated, with maximum tension ($P_o$) at optimal length, 57% higher than that of control muscles. Supplementation did not alter passive length-tension, time-to-peak tension (TPT), or half-relaxation time ($RT_{50}$), however, the maximum rate of tension development (+dT/dt) and the maximum rate of tension fall—dT/dt were increased 47% ($p<0.001$) and 54% ($p<0.001$) respectively by supplementation.

At the lowest afterloads (0.2 $P_0$) the amount of shortening of LVPM from HS122.1A-supplemented rats was 47% increased compared to control rats.

The maximum amount of work (1.24±0.16 $\mu J^*CSA^{-1}*muscle\ length^{-1}$) resulted twice as much as control animals (0.58±0.21 $\mu J^*CSA^{-1}*muscle\ length^{-1}$) Shortening velocity was greater for muscles from HS122.1A rats than for control rats at all loads tested. The maximum velocity of shortening ($V_{max}$) calculated with Hill equations, of 1.52±0.14 $mm^*s^{-1}*muscle\ length^{-1}$ was significantly greater ($p<0.05$) than that of 1.01±0.21 $mm^*s^{-1}*muscle\ length^{-1}$ for control muscle. Muscles from supplemented rats were found to develop a significantly ($p<0.05$) greater tension before shortening velocity was reduced to zero averaging 36.76±8.65 $mN^*mm^{-2}$ compared to 23.35±5.61 $mN^*mm^{-2}$ for LVPM from control rats. Concerning power obtained as the product between shortening velocity an loads lifted, the maximum value (9.24±2.22 $\mu W^*CSA^{-1}*muscle\ length^{-1}$) was twice as high in the HS122.1A-supplemented rats ($p<0.05$) as in control rats (4.44±1.02 $\mu LW^*CSA^{-1}*muscle\ length^{-1}$).

In conclusion HS122.1A supplementation resulted in improved cardiac functions and contractility in the rat.

20 male Wistar rats obtained from Charles River, Italy, were used. Animals were kept in an animal house, under controlled environmental conditions (12-h light-dark cycle, 22-24° C., 40-50% humidity) and received food and water ad libitum.

Animals were randomly assigned to receive daily, by gavage, for 7 weeks, either a blank treatment consisting of carboxy-methyl cellulose (CMC) or HS122.1A, a co-formulation containing (mg/Kg/d in CMC): propionyl-L-carnitine (35.02), coenzyme $Q_{10}$ (2.77), riboflavine (2.77), pantothenic acid (2.77). Ten rats received HS122.1A and ten rats received CMC. CMC is commonly used to facilitate a suspension of pulverised or insoluble substances.

Body Weight Determination

Each animal was daily weighed on a Mettler (Switzerland) balance, accurate to ±1 g, in order to establish the amount of HS122.1A or vehicle to be administered to each rat.

Muscle Preparation and Mounting

After the period of supplementation (7 weeks) the animals were anesthetized by ether and euthanasia followed by rapid excision of the heart. The heart was initially placed in Krebs solution. Under stereomicroscope (16×, Zeiss) left papillary muscle was excised with a small portion of ventricle. Papillary muscle was mounted between two small metallic clips (Fine Science Tools, Vancouver, Canada) and vertically placed in a jacketed perspex chamber (10 ml) containing Krebs solution, with the lower end (the ventricular wall end) attached to a force transducer (Mod.Wp1 Fort 10, 2200 $\mu^*V^*V^{-1}*g^{-1}$, ADInstrument, Pty Ldt, Australia) which was fitted in the chamber. The upper end connected via a carefully straightened steel wire to an isotonic lever of a linear displacement transducer (moment of inertia 35 $g^*cm^{-2}$, breakaway torque<0.1 $g^*cm^{-1}$, Basile Comerio, Italy). The transducer lever arm (fulcrum-organ ring length: 10 cm, operating range: ±15°) was made of a thin wall of carbon fibre conical tube. Lever arm loading was provided by a tungsten alloy cylinder counterweight moving along a scale producing a load variation of 0.01 g/step. Each experiment was carried out with two muscles from control and HS122.1A-supplemented rats respectively, contracting simultaneously in two organ baths. Each preparation was initially allowed to contract isotonically at a frequency of 0.06 Hz under a load of 10 mN while in solution. This initial equilibration period lasted for 40-60 min and was considered complete when mechanical performance had stabilised.

Length-Tensions Recordings

After equilibration period the muscles were set to contract isometrically and stimulated at a frequency of 0.06 Hz. Preliminary determination was made of the optimum length for maximum developed tension production ($L_{max}$). Muscle lengths were altered by incremental steps of 0.1 mm and the muscles were allowed to equilibrate for a period of approximately 5 minutes at each new length. Optimum length ($L_{max}$) was determined as the point of maximum developed tension production during this sequence of increasing muscle lengths. The muscles were next stretched to 1.06 $L_{max}$ and reduced to the selected length by 0.02 $L_{max}$ decrements from 1.06 to 0.94 $L_{max}$. In order to minimize the effects of stress-relaxation muscles were allowed to equilibrate for a period of 5 minutes at each new length. The mechanical properties of this preparation remain relatively stable for many hours and reproducible length-tension curves were obtained.

Force-Velocity Recordings

Upon completion of the isometric recordings and after subsequent 20-30 minutes equilibration period isotonic experiments were performed. The shortening response to electrical stimulation was recorded by classic afterload isotonic technique. Initially, a preload corresponding to resting tension (RT) recorded at $L_{max}$ (see Table 1) was applied to the muscle. The preparations were after-loaded by progressive increments of 20%, 40%, 60%, 80%, 100% $P_0$. At any load, developed tension and shortening were simultaneously recorded.

TABLE 1

(Body and organ weights)

| | Control | Treated |
|---|---|---|
| Initial body weight (g) | 161.2 ± 14.5 | 175.2 ± 10.1 |
| Final body weight (g) | 339.0 ± 20.2 | 338.9 ± 27.9 |
| Heart weight (mg) | 967.3 ± 99.8 | 930.7 ± 80.7 |
| LVPM weight (mg) | 12.4 ± 3.2 | 12.1 ± 1.9 |

Values are mean ± standard deviation. In control and treated group n = 10 animals.

Electrical Stimulation

Electrical stimuli were supplied by parallel platinum electrodes delivering 5 ms square wave pulses at current intensities (8-14 mA) which were 10% greater than the minimum necessary to produce mechanical response. Transverse electrical field stimulation was supplied to the electrodes by high power constant current (Multiplexing pulser booster, Basile, Comerio, Italy) connected to a PowerLab stimulator (ADInstruments, Pty Ldt Australia). Isometric and isotonic twitch tensions were recorded at a frequency of 0.06 Hz.

Solutions

Krebs solution had the following composition (mM): NaCl 123, KCl 6.0, $CaCl_2$ 2.50, $MgSO_4$ 1.2, $NaHCO_3$ 20, $KH_2PO_4$ 1.2, Glucose 11. The solution was continuously aerated with a mixture 95% $O_2$ and 5% $CO_2$ during dissection of the muscles as well as during the actual experiment.

Temperature

The temperature was kept constant at 30±0.5° C. throughout the experiment by circulating water from a termostated tank (Basile, Comerio, Italy) through the jacket around the muscle chamber.

Recording System.

Isometric and isotonic experimental signals were recorded and analysed by a computer (Pentium IV Pro 512 MB ram; the software chart V.4.1.2) equipped with an analogical-to-digital converter program (PowerLab, ADInstruments, Pty Ldt Australia).

Length-Tension Curve Determination

At each increment in length resting and developed tensions were measured. Resting tension was measured from the baseline tension, (determined at minimal increment in tension recorded: 0.01-0.025 mN) in the rest period just before the next change in length. Total tension was measured between peak developed tension and baseline tension, developed tension was measured as difference between total and resting tensions.

Tension values were normalised to cross-sectional area (CSA). The cross-sectional area of each muscle was calculated from the equation A=M/ρL, were M is mass (g), ρ is the density (g/ml) and numerically equal to the specific gravity, and L is the length (mm). The specific gravity of the tissue bathed in Krebs-bicarbonate solution, as determined by pycnometric technique, was 1.056. Muscle length was measured at $L_{max}$.

Force-Velocity and Power-Load Curve Determinations.

A first processing step in analysing experimental shortening waves was the denoising, that is, estimating the unknown signal of interest from the available noisy data. The denoised data was obtained by Daubechies Discrete Wavelet Transform. At each afterload applied, velocity of shortening was taken as peak of velocity obtained by calculating the average of the highest velocities reached by shortening wave. The relation between the velocity of shortening and the load was determined by plotting the developed tension vs. peak velocity of shortening for each afterload. Shortening velocity was normalized to muscle length and was expressed as $mm*s^{-1}*muscle\ length^{-1}$.

Power-load curves were obtained by multiplying force by velocity at each afterload applied.

Statistical Analysis

In order to verify the differences among supplemented and control groups, an analysis of variance (ANOVA) was performed and p<0.05 was considered significant. Length-tension determinations, shortening, shortening velocity, work and power were graphically represented in terms of mean values±S.D.

Results

The general features of animals and LVPM from HS 122.1A-supplemented and control rats are see in table I.

Measurements of heart weight, body weight, and heart weight to body weight ratio between groups showed no difference.

No significant difference was found when muscle length, muscle weight and resultant cross sectional area were compared between HS122.1A-supplemented and control rats.

Isometric Measurements. Length-Tension Determinations.

The effects of HS122.1A on Frank-Starling mechanism of rat papillary muscle are shown in the representative experimental traces and length-tension relationships reported in FIG. 1. Experimental traces (FIG. 1A-B) report the typical active twitch tension recorded on two LVPMs from HS122.1A-supplemented (FIG. 1A) and control rats (FIG. 1B). Muscle length was progressively reduced to the selected length by 0.02 $L_{max}$ decrements from 1.06 to 0.94 $L_{max}$. As shown in the diagram of FIG. 1C, the length-active tension of supplemented muscles increased with peak force ($P_0$) generated at $L_{max}$=36.76±8.65 $mN*mm^{-2}$ that resulted 57% higher if compared with control rats (23.35±5.61 $mN*mm^{-2}$) (p<0.001) (FIG. 1D). Supplementation did not significantly alter the passive length-tension of LVPMs; however the total tension curves were higher (p<0.05) for supplemented rats over the entire range of muscle lengths studied.

Figure 2:
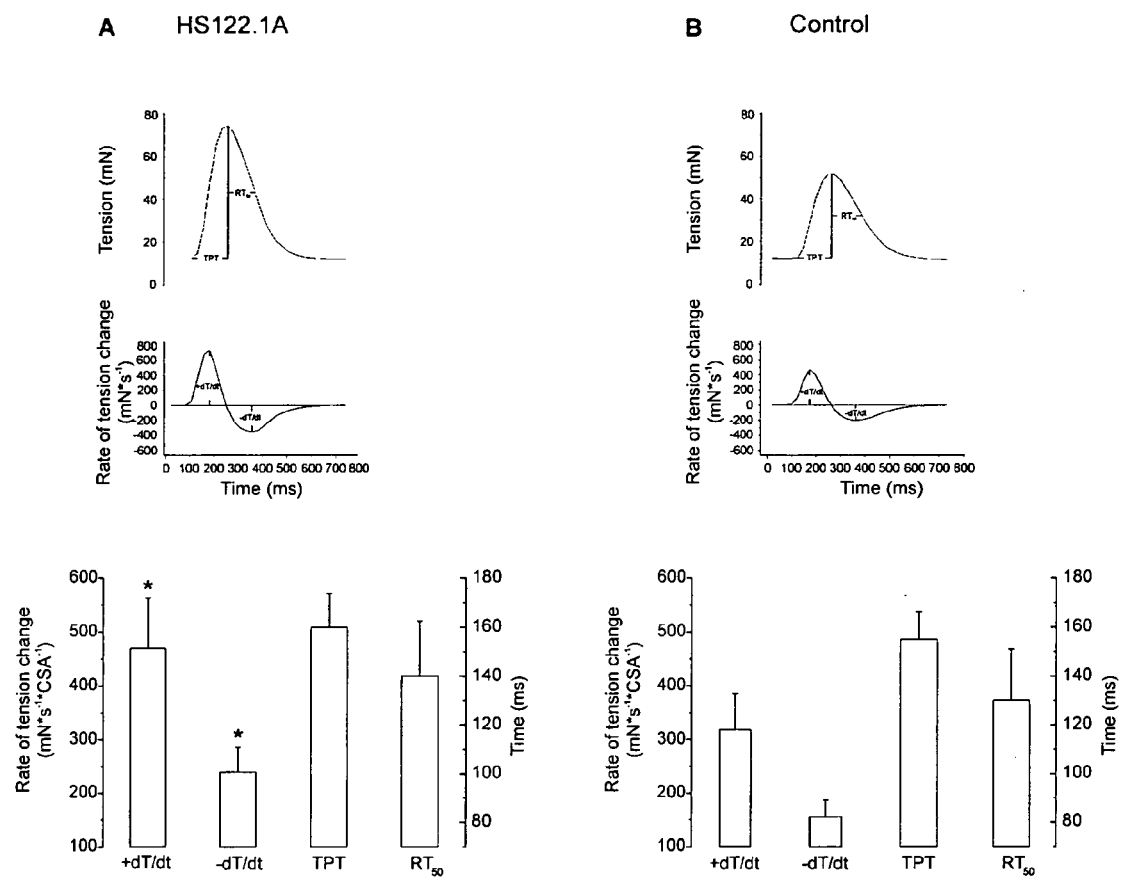
FIG. 2 represents the mechanical parameters obtained in isometric contractions on LVPM from HS122.1A-supplemented (A) and control (B) rats.

A positive inotropic effect of HS122.1A was observed on isometric timing indices. As reported in FIG. 2, the maximum rate of tension development (+dT/dt) and the maximum rate of tension fall (−dT/dt) resulted increased 47% (p<0.001) and 54% (p<0.001) respectively in supplemented rats (FIG. 2A) if compared to control ones (FIG. 2B). Supplementation did not change time-to-peak tension (TPT), and the half-relaxation time ($RT_{50}$).

Figure 3:
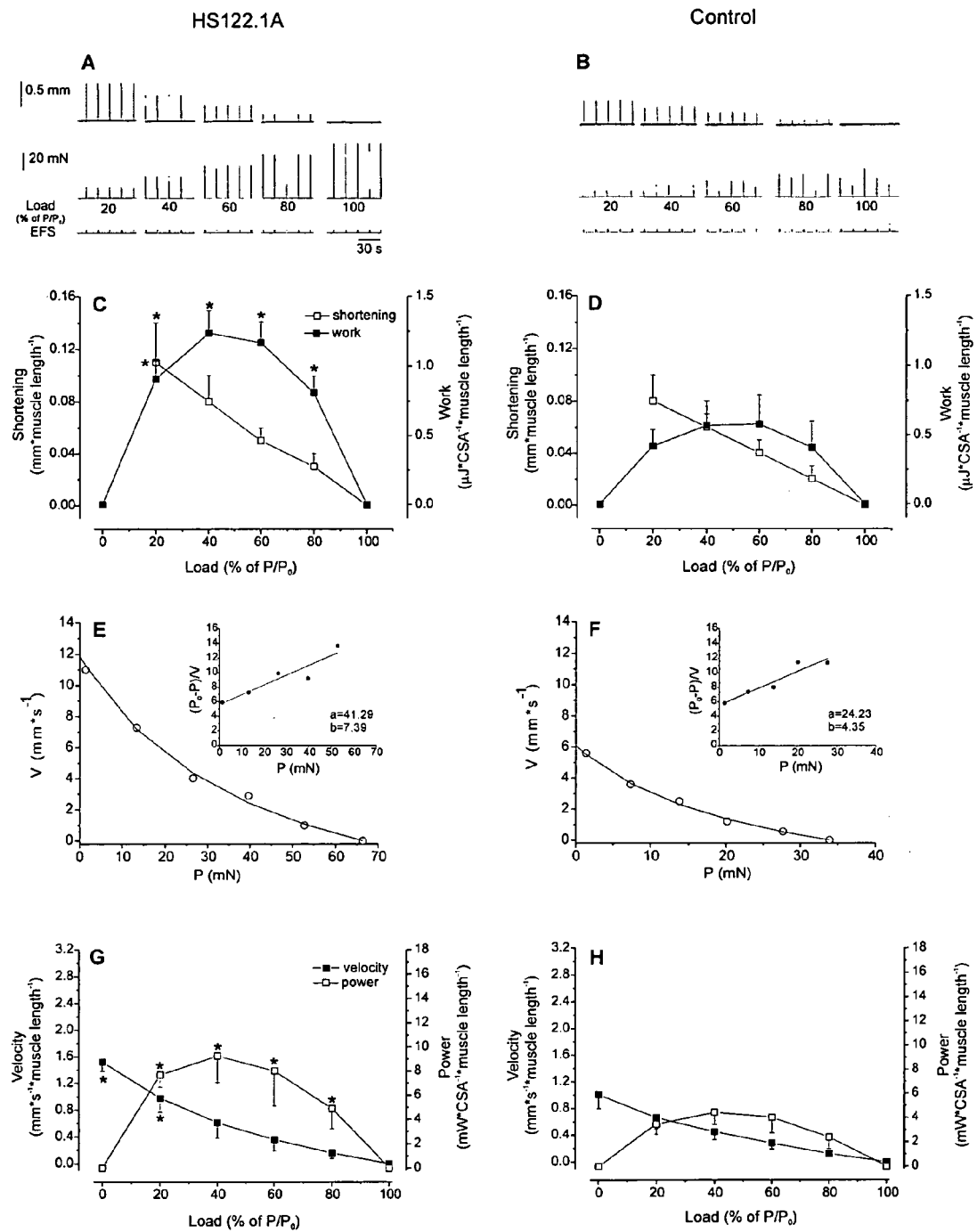
FIG. 3 represents shortening, work, velocity of shortening and power determined on HS122.1A-supplemented and control LVPMs.

Isotonic Measurements. Shortening, Work, Shortening Velocity and Power Determination A positive inotropic effect was also found on isotonic parameters recorded on LVPMs from HS122.1A supplemented rats. FIG. 3 depicts the representative experimental traces of the shortening and the force recorded at various afterloads ranging from 20% to 100% $P_0$ on one LVPM from HS122.1A-supplemented (FIG. 3A) and control rats (FIG. 3B). As shown in FIG. 3C at the lowest afterloads (0.2 $P_0$), the maximum shortening of LVPM from HS122.1A supplemented rats was 47% increased compared to control rats (FIG. 3D) (p<0.05). The maximum amount of work normalised to cross sectional area and muscle length (1.24±0.16 µJ) (FIG. 3C) resulted two time greater (p<0.01) than in control animals (0.58±0.21 µJ) (FIG. 3D). FIG. 3E-F report a velocity of shortening curve determined with Hill equation on a single LVPM from supplemented (FIG. 3E) and control (FIG. 3F) rats. Velocity of shortening was greater for muscles from HS122.1A rats (FIG. 3G) than for control rats (FIG. 3H) at all loads applied. In the supplemented muscles the maximum shortening velocity ($V_{max}$) of 1.52±0.14 mm*s$^{-1}$*muscle length$^{-1}$ was significantly greater (p<0.05) than that of 1.01±0.21 mm*s$^{-1}$*muscle length$^{-1}$ for control muscle. Muscles from supplemented rats were found to develop a significantly (p<0.05) greater tension before shortening velocity was reduced to zero averaging 36.76±8.65 mN*mm$^{-2}$ compared to 23.35±5.61 mN*mm$^{-2}$ for LVPM from control rats. Concerning power obtained as the product between shortening velocity an loads lifted, the maximum value (9.24±2.22 μW*CSA$^{-1}$*muscle length$^{-1}$) was twice as high in the HS122.1A-supplemented rats (p<0.05) (FIG. 3G) as in control rats (4.44±1.02 μW*CSA$^{-1}$*muscle length$^{-1}$) (FIG. 3H).

Discussion

The present results show that treatment with HS122.1A, a co-formulation of Propionyl L-Carnitine, Coenzyme $Q_{10}$, Riboflavin and Pantothenic acid, elicits positive functional changes on mechanical functions of cardiac muscles in the rat. In particular HS122.1A improved the Frank-Starling mechanism increased shortening velocity, shortening, work and power of papillary muscle.

An increase in the total number of contractile filaments may have contributed towards increasing the developed active tension observed in cardiac and smooth muscles. Treatment, however, did not seem to influence contractile filament density, since no significant differences were found in dry weight specimens/body weight ratio between supplemented and control animals. Furthermore fibre damage was possibly minimized by using a portion of the ventricular wall to attach the muscle to the transducer clip.

It is known that maximal shortening velocity is correlated with the rate of ATP hydrolysis, which is catalyzed by myosin ATPase. On a theoretical basis the enhancement of shortening velocity observed in all specimens from the supplemented animals could arise from: 1) an increase in the amount and/or activity of myosin ATPase, 2) an increased availability in ATP in individual muscular contractile cells.

In conclusion our findings indicate that HS 122.1A improves the bioenergetic activity of cardiac muscle cells, possibly on the basis of increased energy production.

The invention claimed is:

1. A method of facilitating skeletal muscles ability to sustain prolonged periods of intense physical activity and providing energy and strengthening to skeletal muscles comprising
administering to individuals engaging in intense and prolonged sporting activities in need thereof a dietary supplement consisting of:
(a) propionyl L-carnitine or a pharmacologically acceptable salt thereof;
(b) coenzyme $Q_{10}$;
(c) riboflavin; and
(d) pantothenic acid; and
facilitating said skeletal muscles ability to sustain said prolonged periods of intense physical activity and providing said energy and strengthening to said skeletal muscles in said individuals.

2. The method of claim 1 wherein the pharmacologically acceptable salt is selected from the group consisting of chloride, bromide, iodide, aspartate, acid aspartate, citrate, acid citrate, phosphate, acid phosphate, fumarate, acid fumarate, glycerophosphate, glucose phosphate, lactate, maleate, acid maleate, mucate, orotate, oxalate, acid oxalate, sulphate, acid sulphate, tartrate, trichloroacetate, trifluoroacetate and methane sulphonate.

3. A method of facilitating skeletal muscles ability to sustain prolonged periods of intense physical activity and providing energy and strengthening to skeletal muscles comprising
administering to individuals engaging in intense and prolonged sporting activities in need thereof a dietary supplement consisting of:
(a) propionyl L-carnitine or a pharmacologically acceptable salt thereof;
(b) coenzyme $Q_{10}$;
(c) riboflavin; and
(d) pantothenic acid;
and at least one of the following components:
(f) an amino acid selected from the group consisting of valine, leucine and isoleucine or mixtures thereof;
(g) a creatine selected from the group consisting of creatine and phosphocreatine or mixtures thereof, and
facilitating said skeletal muscles ability to sustain said prolonged periods of intense physical activity and providing said energy and strengthening to said skeletal muscles in said individuals.

4. The method of claim 1 wherein the weight ratio (a):(b):(c):(d) ranges from 10:0.04:0.08:0.4 to 1:4:4:20.

5. The method of claim 4 wherein the weight ratio (a):(b):(c):(d) ranges from 10:2:2:2 to 1:1:1:5.

6. The method of claim 1 wherein the composition is in a unit dosage form consisting of:
propionyl L-carnitine from 50 mg to 2.000 mg
coenzyme $Q_{10}$ from 5 mg to 200 mg
riboflavin from 5 mg to 200 mg
pantothenic acid from 10 mg to 1.000 mg.

7. The method of claim 1 wherein the composition is in a unit dosage form consisting of:
(a) propionyl L-carnitine from 250 mg;
(b) coenzyme $Q_{10}$ 20 mg;
(c) riboflavin 20 mg; and
(d) pantothenic acid 20 mg.

8. The method of claim 3 wherein the composition is in a unit dosage form consisting of:
(a) propionyl L-carnitine or a pharmacologically acceptable salt thereof;
(b) coenzyme $Q_{10}$;
(c) riboflavin;
(d) pantothenic acid; and
(e) creatine.

* * * * *